United States Patent [19]

Hatano et al.

[11] Patent Number: 5,476,973
[45] Date of Patent: Dec. 19, 1995

[54] STABLE M-VINYLPHENOL COMPOSITION, AND METHODS OF STABILIZING AND PURIFYING M-VINYLPHENOL

[75] Inventors: Rika Hatano, Funabashi; Tadashi Matsumoto, Ohmiya; Teruki Matsukami, Yachiyo, all of Japan

[73] Assignee: Maruzen Petrochemical Co., Ltd., Tokyo, Japan

[21] Appl. No.: 390,571

[22] Filed: Feb. 17, 1995

[30] Foreign Application Priority Data

Mar. 15, 1994 [JP] Japan ..................... 6-043664

[51] Int. Cl.⁶ .................... C07C 27/26; C07C 29/94; C07C 37/88
[52] U.S. Cl. .................... 568/703; 568/724; 568/749; 568/756
[58] Field of Search .................... 568/724, 749, 568/756, 701, 702, 703

[56] References Cited

U.S. PATENT DOCUMENTS 2,570,403  10/1951  Stevens et al. .................... 568/703
3,623,984  11/1972  Carlos .................... 568/701
4,692,544  9/1987  Goerner .................... 568/701

FOREIGN PATENT DOCUMENTS 1235894  3/1967  Germany .................... 568/703

*Primary Examiner*—Werren B. Lone
*Attorney, Agent, or Firm*—Oblon, Spivak, McClelland, Maier & Neustadt

[57] ABSTRACT

Disclosed herein are a stable m-vinylphenol composition comprising m-vinylphenol and tolylene-2,4-diamine and/or N,N-dimethyl-p-phenylenediamine added thereto, a method of stabilizing m-vinylphenol, which comprises adding tolylene-2,4-diamine and/or N,N-dimethyl-p-phenylenediamine to m-vinylphenol, and a method of purifying m-vinylphenol by distillation, which comprises adding tolylene-2,4-diamine and/or N,N-dimethyl-p-phenylenediamine to m-vinylphenol upon the purification of m-vinylphenol by distillation.

6 Claims, No Drawings

STABLE M-VINYLPHENOL COMPOSITION, AND METHODS OF STABILIZING AND PURIFYING M-VINYLPHENOL

BACKGROUND OF THE INVENTION

1. Field of the Invention

The present invention relates to a stable m-vinylphenol composition, and methods of stabilizing and purifying m-vinylphenol.

2. Description of the Background Art m-Vinylphenol is useful as a monomer for producing homopolymers and copolymers having hydroxyl groups in their molecules. Besides, the thus-obtained homopolymers and copolymers having hydroxyl groups in their molecules are rich in reactivity and are hence substances useful in various fields.

However, m-vinylphenol is very unstable compared with vinylbenzene and hence involves a drawback that it tends to cause a polymerization reaction during its handling or treatment such as storage, shipment or purification. In particular, such tendency becomes pronounced at a high temperature. It is therefore necessary to keep m-vinylphenol stable so as not to cause a polymerization reaction upon its handling or treatment such as storage, shipment or purification.

Thus, many investigations as to the inhibition of polymerization of vinylphenols (ortho, meta and para isomers) have heretofore been made. For example, there have been proposed a method in which an alcohol having or not having a substituent group or a phenol having or not having a substituent group is added as a polymerization inhibitor (Japanese Patent Publication No. 29137/1976), a method in which an aromatic nitro compound or a sulfoxide is added as a polymerization inhibitor (Japanese Patent Publication No. 41577/1979), a method in which an ether, a ketone or a sulfone is added (Japanese Patent Publication No. 16129/1980) and a method in which a nitrile is added (Japanese Patent Publication No. 24771/1982). Concerning the inhibition of polymerization of m-vinylphenol, it has also been proposed to add an aliphatic amine such as trimethylamine, an aromatic amine such as o- or p-phenylenediamine or aniline, a heterocyclic amine such as pyridine, quinoline or piperidine, phenylhydrazine, or the like (U.K. Patent No. 670,502). All these various compounds used as the polymerization inhibitors for vinylphenols or m-vinylphenol have been insufficient in the polymerization-inhibiting effect and hence not satisfactory.

SUMMARY OF THE INVENTION

It is thus an object of the present invention to provide a substance having an excellent polymerization-inhibiting effect on m-vinylphenol, and methods of stabilizing and purifying m-vinylphenol by using this substance.

With the foregoing circumstances in view, the present inventors have carried out an extensive investigation with a view toward achieving the above object. As a result, it has been found that tolylene-2,4-diamine and N,N-dimethyl-p-phenylenediamine have an excellent polymerization-inhibiting effect on m-vinylphenol, that these compounds are far excellent in the polymerization-inhibiting effect on m-vinylphenol compared with the various polymerization inhibitors for vinylphenols or m-vinylphenol, which have been proposed to date, and particularly, even as compared with o- or p-phenylenediamine having a similar structure, and that tolylene-2,4-diamine and N,N-dimethyl-p-phenylenediamine are stable compounds, and hence sufficiently exhibit the polymerization-inhibiting effect without deterioration even when used in, for example, the purification of m-vinylphenol by distillation, thus leading to completion of the present invention. Further, the present inventors have found that tolylene-2,6-diamine or tolylene-3,4-diamine, which is an isomer of tolylene-2,4-diamine is poor in the polymerization-inhibiting effect, and that N-methyl-p-phenylenediamine different in the number of the methyl group substituted from N,N-dimethyl-p-phenylene-diamine is also poor in the polymerization-inhibiting effect.

In an aspect of the present invention, there is thus provided a stable m-vinylphenol composition comprising m-vinylphenol and tolylene-2,4-diamine and/or N,N-dimethyl-p-phenylenediamine added thereto.

In another aspect of the present invention, there is also provided a method of stabilizing m-vinylphenol, which comprises adding tolylene-2,4-diamine and/or N,N-dimethyl-p-phenylenediamine to m-vinylphenol.

In a further aspect of the present invention, there is provided a method of purifying m-vinylphenol by distillation, which comprises adding tolylene-2,4-diamine and/or N,N-dimethyl-p-phenylenediamine to m-vinylphenol upon the purification of m-vinylphenol by distillation.

According to the present invention, the addition of tolylene-2,4-diamine and/or N,N-dimethyl-p-phenylene-diamine as a polymerization inhibitor permits m-vinylphenol to favorably keep its stability upon purification, storage, shipment or the like.

The above and other objects, features and advantages of the present invention will be readily appreciated as the same becomes better understood from the preferred embodiments of the present invention, which will be described subsequently in detail, and from the appended claims.

DETAILED DESCRIPTION OF THE PREFERRED EMBODIMENTS

According to the present invention, m-vinylphenol can be stabilized irrespective of its purity. Therefore, those having a high purity or containing impurities in plenty, for example, high-purity m-vinylphenol as a commercial product and crude m-vinylphenol obtained from its production process by dehydrogenation of m-ethylphenol and containing impurities in plenty, may be stabilized.

More specifically, m-vinylphenol is generally produced by dehydrogenation of m-ethylphenol. In this dehydrogenation process, crude m-vinylphenol containing 10–70 wt. % of m-ethylphenol is provided. And, the inhibition of polymerization may also be aimed at such crude m-vinylphenol.

Tolylene-2,4-diamine and N,N-dimethyl-p-phenylene-diamine as the polymerization inhibitors in the present invention may be used either singly or in any combination thereof. The amount of these compounds to be used is preferably 0.1–50 wt. % (hereinafter indicated merely by "%"), particularly 5–30% based on the weight of m-vinyl-phenol irrespective of the concentration of m-vinylphenol. If the amount to be used is less than 0.1%, a sufficient polymerization-inhibiting effect cannot be expected. On the other hand, their use in an amount greater than 50% is not preferable from an economical viewpoint because an improvement corresponding to such an amount in the polymerization-inhibiting effect cannot be expected.

In order to inhibit the polymerization of m-vinyl-phenol to stabilize it, it is only necessary to add and mix tolylene- 2,4-diamine and/or N,N-dimethyl-p-phenylene-diamine in the above-described amount to and with m-vinylphenol upon its various treatments or handlings such as purification, storage and shipment.

In particular, m-vinylphenol causes polymerization upon its purification by distillation. When the above-described stabilizer is added prior to the distillation, however, the polymerization can be inhibited, thereby obtaining high-purity m-vinylphenol at a high yield.

In this purification method by distillation, any known means may be used as a distillation means itself. No particular means are hence required. For example, in the case of batch distillation, tolylene-2,4-diamine and/or N,N-dimethyl-p-phenylenediamine are added to m-vinylphenol to require purification. The resultant mixture is then subjected to batch distillation at a bottom temperature of 150° C. or lower, preferably 120° C. or lower, whereby purified m-vinylphenol can be obtained. In the case of continuous distillation, tolylene-2,4-diamine and/or N,N-dimethyl-p-phenylenediamine are added to m-vinylphenol to require purification. The resultant mixture is then fed to the first distilling column to distill it at a bottom temperature of 150° C. or lower, preferably 120° C. or lower. The resulting bottom component is fed to the second distilling column to distill it at a bottom temperature of 150° C. or lower, preferably 120° C. or lower, whereby purified m-vinylphenol can be obtained from the tops of the columns.

In order to avoid forming a polymer of m-vinylphenol during distilling operation, it is desirable to lower the bottom temperature and shorten residence time in a distilling column as much as possible. For doing so, it is preferable to use a packed column or a thin-film distiller, which is low in pressure loss and short in residence time, rather than a multistage distilling column, which is high in pressure loss and long in residence time.

Tolylene-2,4-diamine and/or N,N-dimethyl-p-phenylene-diamine added to m-vinylphenol in the present invention can be removed simply by distillation. For example, m-vinylphenol containing tolylene-2,4-diamine and/or N,N-dimethyl-p-phenylenediamine is fed to a distillatory apparatus to distill it at a bottom temperature of 150° C. or lower, preferably 120° C. or lower, whereby still residue containing tolylene-2,4-diamine and/or N,N-dimethyl-p-phenylenediamine in plenty can be obtained from the bottom, and m-vinylphenol can be obtained from the top of the column, respectively.

The present invention will hereinafter be described in detail by reference to the following examples and comparative examples. However, it should be borne in mind that this invention is not limited to these examples.

EXAMPLE 1

Tolylene-2,4-diamine was added as a polymerization inhibitor to m-vinylphenol having a purity of 97% and containing 3% of m-acetoxystyrene to give a concentration of 0.5% based on m-vinylphenol, thereby preparing a composition. This composition was placed in a test tube made of glass. After air in the interior of the test tube was purged with nitrogen gas, the upper part of the test tube was heat-sealed. The thus-sealed tube was placed in an oil bath kept at 100° C. After 2 hours, the upper part of the test tube was unsealed, and the contents were subjected to gel permeation chromatography. As a result, no formation of the dimer and still higher polymers of m-vinylphenol was recognized.

EXAMPLE 2

A test was conducted in the same manner as in Example 1 except that N,N-dimethyl-p-phenylenediamine was used as a polymerization inhibitor in place of tolylene-2,4-diamine. As a result, no formation of the dimer and still higher polymers of m-vinylphenol was recognized.

Comparative Example 1

A test was conducted in the same manner as in Example 1 except that no polymerization inhibitor was added. As a result, it was found that the dimer and still higher polymers of m-vinylphenol were formed in an amount of 22.6%.

Comparative Example 2

A test was conducted in the same manner as in Example 1 except that p-t-butylcatechol was added as a polymerization inhibitor in place of tolylene-2,4-diamine. As a result, it was found that the dimer and still higher polymers of m-vinylphenol were formed in an amount of 1.7%.

Comparative Example 3

A test was conducted in the same manner as in Example 1 except that p-phenylenediamine was added as a polymerization inhibitor in place of tolylene-2,4-diamine. As a result, it was found that the dimer and still higher polymers of m-vinylphenol were formed in an amount of 4.8%.

Comparative Example 4

A test was conducted in the same manner as in Example 1 except that o-phenylenediamine was added as a polymerization inhibitor in place of tolylene-2,4-diamine. As a result, it was found that the dimer and still higher polymers of m-vinylphenol were formed in an amount of 7.5%.

Comparative Example 5

A test was conducted in the same manner as in Example 1 except that hydroquinone was added as a polymerization inhibitor in place of tolylene-2,4-diamine. As a result, it was found that the dimer and still higher polymers of m-vinylphenol were formed in an amount of 6.9%.

Comparative Example 6

A test was conducted in the same manner as in Example 1 except that m-aminophenol was added as a polymerization inhibitor in place of tolylene-2,4-diamine. As a result, it was found that the dimer and still higher polymers of m-vinylphenol were formed in an amount of 5.1%.

Comparative Example 7

A test was conducted in the same manner as in Example 1 except that tolylene-2,6-diamine was added as a polymerization inhibitor in place of tolylene-2,4-diamine. As a result, it was found that the dimer and still higher polymers of m-vinylphenol were formed in an amount of 1.1%.

Comparative Example 8

A test was conducted in the same manner as in Example 1 except that tolylene-3,4-diamine was added as a polymerization inhibitor in place of tolylene-2,4-diamine. As a result, it was found that the dimer and still higher polymers of m-vinylphenol were formed in an amount of 9.5%.

Comparative Example 9

A test was conducted in the same manner as in Example 1 except that N-methyl-p-phenylenediamine was added as a polymerization inhibitor in place of tolylene-2,4-diamine. As a result, it was found that the dimer and still higher polymers of m-vinylphenol were formed in an amount of 5.1%.

EXAMPLE 3

A mixture obtained by adding tolylene-2,4-diamine as a polymerization inhibitor to 200 g of m-vinylphenol containing 72.3% of m-ethylphenol to give a concentration of 0.5% based on m-vinylphenol was subjected to batch distillation under reduced pressure by means of a 15-stage Oldershaw type distillatory apparatus. A reflux ratio, bottom temperature and top pressure were 20, 113°–120° C. and 1 mmHg, respectively. Upon elapsed time of 5 hours from the beginning of the distillation, still residue containing 91% of m-vinylphenol was obtained. No formation of the dimer and still higher polymers of m-vinylphenol was recognized in the still residue. Further, no formation of the dimer and still higher polymers of m-vinylphenol was also recognized in distillate. Tolylene-2,4-diamine remained in the still residue, and its existence was not recognized in the distillate. The recovery of m-vinylphenol was 95%.

Comparative Example 10

A test was conducted in the same manner as in Example 3 except that no polymerization inhibitor was added. As a result, still residue containing 62% of m-vinylphenol was obtained. The still residue contained 29% of the dimer and still higher polymers of m-vinylphenol. No formation of the dimer and still higher polymers of m-vinylphenol was recognized in distillate. The recovery rate of m-vinylphenol was 67%.

What is claimed is:

1. A stable m-vinylphenol composition comprising m-vinylphenol and tolylene-2,4-diamine and/or N,N-dimethyl-p-phenylenediamine added thereto.

2. The stable m-vinylphenol composition according to claim 1, wherein the amount of tolylene-2,4-diamine and/or N,N-dimethyl-p-phenylenediamine to be added is 0.1–50 wt. % based on the weight of m-vinylphenol.

3. A method of stabilizing m-vinylphenol, which comprises adding tolylene-2,4-diamine and/or N,N-dimethyl-p-phenylenediamine to m-vinylphenol.

4. The method according to claim 3, wherein the amount of tolylene-2,4-diamine and/or N,N-dimethyl-p-phenylenediamine to be added is 0.1–50 wt. % based on the weight of m-vinylphenol.

5. A method of purifying m-vinylphenol by distillation, which comprises adding tolylene-2,4-diamine and/or N,N-dimethyl-p-phenylenediamine to m-vinylphenol upon the purification of m-vinylphenol by distillation.

6. The method according to claim 5, wherein the amount of tolylene-2,4-diamine and/or N,N-dimethyl-P-phenylenediamine to be added is 0.1–50 wt. % based on the weight of m-vinylphenol.

* * * * *